(12) United States Patent
Valentini et al.

(10) Patent No.: US 7,077,297 B1
(45) Date of Patent: Jul. 18, 2006

(54) METHOD FOR PREPARATION OF BIOCIDES MIXED WITH CARBON DIOXIDE IN A PRESSURIZED CONTAINER

(75) Inventors: Giorgio Valentini, Pisa (IT); Claudio Menicagli, Pisa (IT)

(73) Assignee: Abiogen Pharma S.p.A., Pisa (IT)

( * ) Notice: Subject to any disclaimer, the term of this patent is extended or adjusted under 35 U.S.C. 154(b) by 0 days.

(21) Appl. No.: 10/018,912

(22) PCT Filed: Jun. 23, 2000

(86) PCT No.: PCT/EP00/05836

§ 371 (c)(1),
(2), (4) Date: Dec. 18, 2001

(87) PCT Pub. No.: WO01/00030

PCT Pub. Date: Jan. 4, 2001

(30) Foreign Application Priority Data

Jun. 25, 1999 (IT) .............................. MI99A1416

(51) Int. Cl.
*B65D 83/00* (2006.01)

(52) U.S. Cl. .................. 222/402.1; 222/399; 422/28; 210/754; 210/756; 424/405; 424/661; 424/722

(58) Field of Classification Search ..............
222/402.1–402.25, 399, 394; 424/47, 76.2, 424/76.3, 76.8, 45, 405, 661, 688, 43, 665, 424/700, 722; 422/28, 29, 33, 37, 292, 295, 422/305, 306; 137/268; 210/754, 756, 205, 210/764
See application file for complete search history.

(56) References Cited

U.S. PATENT DOCUMENTS

| | | | | |
|---|---|---|---|---|
| 3,084,995 A | * | 4/1963 | Grubitsch | 423/265 |
| 3,650,405 A | * | 3/1972 | Morrison | 210/241 |
| 3,666,668 A | * | 5/1972 | Klausner | 424/45 |
| 3,896,213 A | * | 7/1975 | Hirdler | 423/232 |
| 3,943,261 A |   | 3/1976 | Amon | |
| 3,972,691 A | * | 8/1976 | Fukushima et al. | 95/39 |
| 4,035,483 A | * | 7/1977 | Bunyan | 424/665 |
| 4,084,747 A | * | 4/1978 | Alliger | 422/20 |
| 4,104,190 A | * | 8/1978 | Hartshorn | 252/187.21 |
| 4,105,253 A | * | 8/1978 | Showalter | 299/4 |
| 4,122,978 A | * | 10/1978 | Guimond et al. | 222/402.1 |
| 4,162,765 A | * | 7/1979 | Riccio | 239/337 |
| 4,361,471 A | * | 11/1982 | Kosarek | 210/748 |
| 4,431,120 A | * | 2/1984 | Burger | 222/192 |
| RE31,779 E | * | 12/1984 | Alliger | 252/187.23 |
| 4,498,978 A | * | 2/1985 | Frame | 208/207 |
| 4,990,334 A | * | 2/1991 | Longino et al. | 424/401 |
| 5,031,252 A | * | 7/1991 | Oyama | 4/233 |

(Continued)

FOREIGN PATENT DOCUMENTS

DE         19706842        8/1998

(Continued)

*Primary Examiner*—Frederick C. Nicolas
(74) *Attorney, Agent, or Firm*—Bucknam and Archer; Joseph J. Orlando

(57) ABSTRACT

This invention relates to a method for the preparation and metering of substances, mixtures of substances and/or compounds in general, characterized by bacteriostatic and/or bactericidal activity, using a single pressurized container in which the substances, mixtures of substances and/or compounds in general are mixed with carbon dioxide in the form of vapor, liquid/vapor mixture or supercritical fluid for the purpose of mixing, dissolving, storing and dispensing at constant predetermined doses. The invention also relates to pressure containers suitable for dispensing the substances in accordance with the invention.

7 Claims, 2 Drawing Sheets

U.S. PATENT DOCUMENTS

| | | | |
|---|---|---|---|
| 5,043,175 A * | 8/1991 | Bayley et al. | 426/318 |
| 5,044,524 A * | 9/1991 | Pistek | 222/212 |
| 5,141,531 A * | 8/1992 | Parrish | 95/126 |
| 5,185,161 A * | 2/1993 | Davidson et al. | 424/665 |
| 5,312,389 A * | 5/1994 | Theeuwes et al. | 604/892.1 |
| 5,520,310 A * | 5/1996 | Bauer et al. | 222/402.2 |
| 5,611,937 A | 3/1997 | Jarocki | |
| 5,631,300 A * | 5/1997 | Wellinghoff | 514/772.3 |
| 5,948,742 A * | 9/1999 | Chang et al. | 510/191 |
| 6,123,237 A * | 9/2000 | Lasserre et al. | 222/402.21 |

FOREIGN PATENT DOCUMENTS

| | | | |
|---|---|---|---|
| EP | 0404015 | | 12/1990 |
| GB | 480176 | * | 2/1938 |
| GB | 1412282 | * | 2/1972 |
| GB | 2101225 A | * | 1/1983 |
| JP | 63130190 A | * | 6/1988 |
| JP | 6277268 | | 10/1994 |
| JP | 2533039 | | 9/1996 |
| RU | 1803127 | | 3/1993 |

* cited by examiner

METHOD FOR PREPARATION OF BIOCIDES MIXED WITH CARBON DIOXIDE IN A PRESSURIZED CONTAINER

FIELD OF APPLICATION

This invention relates to a method for the preparation of substances, mixtures of substances and/or compounds in general having a disinfectant and biocide function, which are mixed, preserved, dissolved and metered by a single pressurised container in the presence of carbon dioxide in the form of a vapour, liquid/vapour mixture or supercritical fluid.

One of the most stringent requirements in the field of disinfection practices is to have substances that are effective, safe, and such to be metered in a controlled way with predetermined efficacy.

For this purpose, the substances used must be stable under storage.

Various attempts have been made to prepare compounds and mixtures with a biocide action, deliver them with the maximum simplicity and under safe conditions and maintain their dose constant, without deterioration of the said substances during storage, but the various problems have never been solved completely and simultaneously.

PRIOR ART

The oxidizing action of chlorine gas probably constitutes the first large-scale application of a biocide in the water treatment. Chlorine gas and the precursors which can produce chlorine gas under the conditions of use have great merits in terms of efficacy, but also a number of limitations in terms of applications.

In the field of disinfection of water intended for human consumption, in which chlorine compounds are extensively used, one of the most evident limitations on the use of this biocide is the inevitable alteration in the taste of the treated water deriving from the presence of chlorine in the amounts required to ensure biocide effect.

In addition, there are scientific evidences that chlorine reacts with the organic matter present in the water to produce traces of organo-chlorine compounds (trihalomethanes or, more generally, AOX) which are very critical from the toxicological point of view due to the recognized cancer-producing activity.

It would therefore be highly desirable to meet hygienic standard of the water using the lowest amounts of chlorine.

In the field of the treatment of swimming pool water the simultaneous delivering of chlorine and carbon dioxide, using two separate pressurized cylinders feed to a special dispersion head, has been patented (see U.S. Pat. No. 3,650,405, issued to Morrison). By this technique a better dispersion and a higher efficiency of chorine is achieved.

This system, as every system in which the presence of chlorine gas under pressure is concerned, shows a number of problems related, first, to safety aspects. Additional problems concern technical and operational construction of the plants and devices used for chorine dispensing, the complexity of obtaining mixtures with a constant active chlorine content, and the difficulty to meter these mixtures in a constant, uniform manner.

U.S. Pat. No. 3,943,261 describes a process for water disinfection and carbonation, wherein the disinfectant from a container is mixed with $CO_2$ in a carbonator under pressure.

U.S. Pat. No. 5,611,937 which is an improvement over U.S. Pat. No. 3,943,261 discloses an apparatus and method for treating water from a local supply, wherein the water is mixed with a chlorine disinfectant and introduced into a holding vessel maintained at ambient pressure, into which $CO_2$ is added.

U.S. Pat. No. 5,043,175 discloses a method and apparatus for sterilisation of animal feed, wherein vaporised chlorinated water produces a mixture of chlorine, gas, steam, and products of combustion which are intimately contacted with the feed product in a mixer conditioner.

JP 06 277 268 A, JP 02 533 039 B and SU 1 803 127 disclose sterilisation plants comprising, inter alia, separate tanks for different substances to be mixed in a sterilising chamber or in an ejection mixer.

EP 0 404 015 describes a disinfection apparatus comprising a carbon dioxide cylinder (10) and a disinfectant composition tank (14), both connected to a spry gun (15) for delivering the disinfectant composition by means of the vaporised carbon dioxide.

GB 480 176 dating back to 1936, discloses a method of purifying air by the dissemination of a hypochlorite solution. The liquid solution is sprayed by a supply of air under pressure as from a cylinder, which can have a definite carbon dioxide content. However the hypochlorite solution is not contained in the cylinder.

BRIEF DESCRIPTION OF THE DRAWINGS

Objects and features of the present invention will become apparent from the following description of the invention considered in connection with the accompanying drawings, in which.

DESCRIPTION OF THE INVENTION

Figure 1:
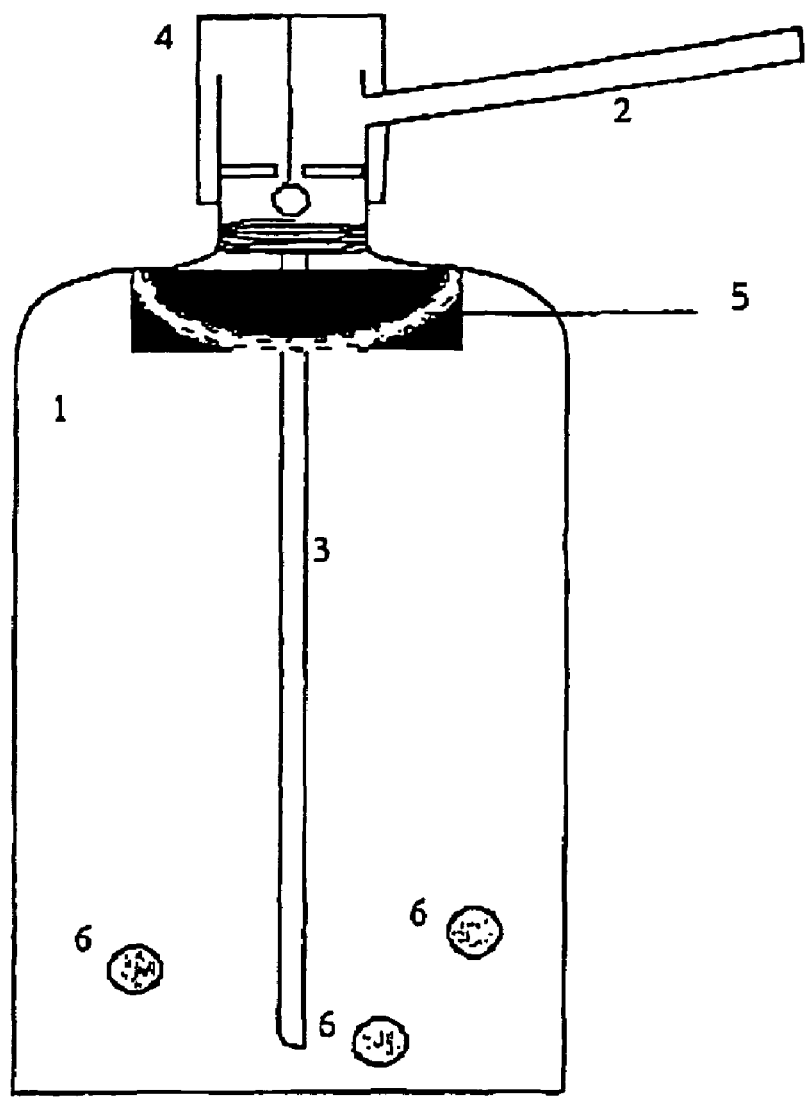
FIG. 1 shows a container suitable for the regulated delivery of a biocide in accordance with the present invention.

This invention relates to a method for the delivering of disinfectants and biocides which consists of mixing the said substances with carbon dioxide in the form of a vapour, a liquid/vapour mixture or supercritical fluid, in a single pressurised container.

The invention also relates to pressurised containers designed to meter and deliver the mixture of carbon dioxide and disinfecting compounds.

Among the different fields in which the invention can be positively and originally applied, the following ones can be taken as representative examples:

disinfection of drinking water (for human and animal consumption, including aquaria)

disinfection of private and sanitary areas (living quarters, swimming pools, public baths, air-conditioning systems, walls and floors, toilets, chemical toilets, waste water, hospital waste, soil or other surfaces, such as gymnasiums and school classrooms)

veterinary hygiene (including hygiene both for animals and for disinfection of the areas in which animals are housed, kept or transported, and for the treatment of waste water and dung from animal breeding units)

human and animal nutrition (in the disinfection of equipment, containers, eating utensils, surfaces or piping used for the production, transport, storage or consumption of food, animal feed or drinks, including drinking water, intended for human or animal consumption)

storage of products in cans, cling-film or wrappings (control of deterioration caused by micro-organisms in foodstuffs, paints, plastics, sealants, adhesives, binders, paper, objets d'art, etc.)

preservation of wood, fibres, leather, rubber and polymers (control of microbiological deterioration)

preservation of masonry, for liquids in industrial treatment and cooling systems, in lubricants (also emulsified) and fluids used in industrial processes (e.g. preservation of water or other fluids used in industrial cooling and treatment systems involving the control of micro-organisms, algae and molluscs)

preservation against the formation of slimy substances control of harmful animals control of fouling (by organisms on boats, aquaculture equipment or other structures used in water)

embalming and taxidermy (disinfection and preservation of corpses and parts thereof).

Examples of compounds with an antibacterial and disinfecting action usable in accordance with the invention include chlorine gas, compounds able to generate chlorine (such as alkali or alkaline-earth hypochlorites, preferably sodium or calcium hypochlorite, or products commonly known by the trademarks Chloramine T and Amuchina, or other organic chlorides), formaldehyde and quaternary ammonium salts, as far as any compound having biocide activity which is compatible with carbon dioxide.

When chlorine gas is used, it is advisable to add a hygroscopic anhydrous salt to the container to adsorb any moisture present and prevent the formation of hydrochloric acid by hydrolysis.

The use of mixtures of chlorine or hypochlorites is particularly preferred.

The method to which the invention relates offers considerable advantages with respect to the known processes.

Firstly, it has been demonstrated that carbon dioxide not only acts as a solvent, propellant and mixing agent, but also increases the disinfecting power of chlorine in particular, in a synergic way. It is therefore possible, in the presence of carbon dioxide, to achieve the same effect in biocidal (bactericidal, germicidal, fungicidal or algicidal) activity with concentrations of chlorine or other active substances which are smaller than usual. This overcomes completely the problems arising from high residual concentrations of chlorine.

Secondly, carbon dioxide enables the disinfectant substances to be stabilised for a long time, as they are stored in an inert, sterile environment.

Finally, carbon dioxide allows to obtain effective dispersal of the active compound in the receiving medium.

The concentration of the biocides can be modulated in a broad range of values by the composition of the mother mixture formed by carbon dioxide and the biocide itself and adequate metering of the same.

The use of sodium or calcium hypochlorites mixed with carbon dioxide produces a solution under pressure which can be metered very simply and accurately. By means of the propellant action of carbon dioxide it is possible to introduce the disinfectant, in a more active formulation, also into conventional carbonating units or water distribution lines operating under pressure.

Mixtures of carbon dioxide and chlorine compounds are prepared in exactly the same way as other mixtures of compressed gases, liquefied compressed gases or gas/liquid blends.

The proposed technique is also suitable for preparing a wide variety of organic or inorganic mixtures with biocide properties in a liquid, semifluid, paste, gel or solid form.

The viscosity of these systems can be modulated on the basis of the final conditions of application of the product.

The method can be used also for extemporary and quick preparation of disinfectant solutions to clean and sterilise articles and surfaces contaminated by biological agents.

Application of the method object of this invention in particular solves the problems connected with the use of chlorine gas or compounds capable of releasing chlorine.

In fact, it is known that sodium or calcium hypochlorites solutions are irritant, and that chlorine gas is toxic.

However, the use of these biocides already diluted in carbon dioxide in a single container drastically reduces the risks associated with the storage and handling of these substances.

It also solves the problem of excesses of chlorine and/or its derivatives remaining in the water subjected to disinfection treatment.

The method of the invention provides hygienically suitable water and/or drinks with very low doses of chlorine, at levels which do not affect odour and flavour of the water.

The pressurised mixtures of carbon dioxide according to the invention can be contained in bottles or tanks of various shapes and volumes, as required.

In one of the preferred embodiments of the invention the containers for said mixtures are metal cylinders, canisters or ampoules suitable to withstand internal pressure.

Metal cylinders usually having large capacity (15–200 liters) and intended, for example, for sanitation of swimming pools or other large-size plants, can contain, by way of example, 50 to 500 g of chlorine gas or 1 to 10 kg of a sodium hypochlorite solution containing 7% w/w of active chlorine together with carbon dioxide in amounts ranging from 10 to 100 kg. By means of said systems, for example, the hygienic control of a medium-size swimming pool (typically containing about 3000 $m^3$ of water) would be guaranteed for a time from 1 to 3 weeks, depending of the size and the content of the pressurised tank.

In case of canisters of smaller capacity (1 to 10 liters), intended for sanitation of small, even domestic, plants or small-size vessels such as aquaria, they can contain sodium hypochlorite solutions with 7% w/w active chlorine in amount of 5 to 100 mg, or 0.5 to 10 mg of chlorine gas, together with carbon dioxide in amounts from 5 to 100 g.

An example of a cylinder suitable for the purposes of the invention is shown in FIG. 1. This is a reinforced container (1) with a spout (2) for emission of the biocidal mixture contained in it, manually regulated by pressing a button (4) connected to a suction tube (3) through which the product is expelled. Protective netting (5) and steel balls (6) to facilitate agitation and mixing of the components could be added for particularly viscous products.

In one embodiment of the invention said cylinder can be used also for delivering gel substances having anti-mould action; in this case the cylinder will contain, by way of example, 50 to 200 g of silica, 10 to 50 g of borax, 5 to 20 g of soap powder, 400 to 600 ml of a sodium hypochlorite solution with 7% w/w active chlorine, 200 to 500 ml of water and 20 to 50 g of carbon dioxide.

By this method a simple system delivering an anti-mould gel is obtained, said gel acting almost instantaneously when distributed on moulded areas. The gel has a very effective anti-mould activity because the contact of the active substances with the surface can be prolonged until any mould has been destroyed.

The size of the pressurized containers for chlorine mixtures may depend on the size of the receiving vessel (which may be a swimming pool, for example, or a bottle) or on the delivery system, which may dispense a single dose (e.g. for the treatment of a single bottle) or a multiple dose (as in the case of maintenance of certain characteristics in swimming pool water or domestic water).

The product can be metered from these containers:

directly into the final receiving medium into another container which acts as a mixer/metering unit, and may already contain some of the constituents of the formulation.

Single-dose containers will typically consist of ampoules or vials made of metal or another material able to withstand internal pressure, fitted with a sealed septum which is perforated at the time of connection with a delivery system or a receiving vessel. Perforation of the septum allows the complete emptying out of the vial.

These systems are usually prepared starting from a master mixture made in a stirred reactor wherein the predetermined weights and volumes of the constituents in the form of a gas, vapour, solid, liquid or paste have been loaded. In the case of constituents in the gaseous or vapour state, the pressurised carbon dioxide must be fed to the reactor simultaneously; if the constituents are in a different physical state, it is fed subsequently.

By means of the internal pressure of the reactor, which is equipped with devices designed to guarantee uniform delivery of the contents, the individual ampoules or vials can be filled before application of the sealed septum.

As an alternative to pressurized loading, the mixture of liquid or solid constituents can be metered into each ampoule and then pressurized with carbon dioxide.

The size of this type of containers can also be very small, as is the case with those intended for the extemporary preparation of disinfectant solutions in soda siphons (generally of 1 liter capacity), where the vial volumes range around 10 ml; the vial will contain, by way of example, 0.1 to 2 mg of chlorine gas or 5 to 20 mg of 7% w/w active chlorine sodium hypochlorite solution, or other biocides, together with carbon dioxide in amounts ranging from 5 to 9 g.

The method (with the indicated dosages) can be used to make small single-dose vials to be used with an ordinary soda siphon to prepare carbonated drinks which are guaranteed to be hygienic, or simply to sanitize impotable water.

By adequately changing the capacities of the containers, and therefore the amounts of the biocides and carbon dioxide contained therein, it is also possible to obtain systems for dispensing multiple doses. These containers will be in the form of vials or ampoules or cylinders made of metal or other materials able to withstand internal pressure, and will be simply fitted with a sealed septum or other device which allows connection with a suitable metering system, possibly interlocked with a specifically programmed automatic control system.

The container is emptied by degrees, either continuously or discontinuously, depending on the type of delivery required.

This kind of solution requires devices designed to ensure that the mixture delivered has constant characteristics over time in terms of quality and composition, which are particularly stringent requirements in all cases in which controlled sterilising conditions are necessary (swimming pool water, water distributed for human consumption, etc.).

If the containers are fitted with sealed septa, the packaging procedure will be identical to that of single-dose systems.

If the containers are fitted with a connector device (such as a tap), the various operations can be performed in two separate sequences:

a. loading of constituents of the mixture into the container without the tap; fitting of tap; pressurisation with carbon dioxide (possibly after creating vacuum in the container)

b. creation of vacuum in the container after fitting the tap; suction of the constituent mixture formed separately together with carbon dioxide (this criterion is essential in the case of gaseous or vapour mixtures); possibly followed by further pressurization with carbon dioxide.

For special applications, the containers used for the invention can be in the shape of a syringe for rapid blowing and injection.

Figure 2:
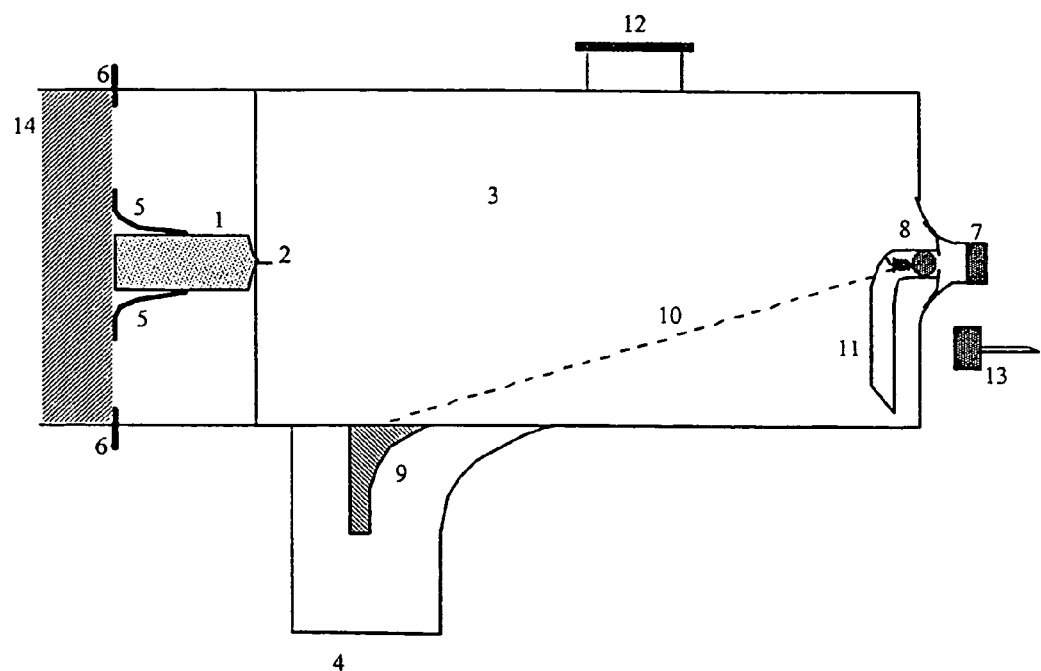
FIG. 2 shows a syringe type device for the delivery of a biocide in accordance with the invention.

FIG. 2 shows a pistol-shaped syringe in which a screwing unit (14) with a travel stop (6) is fitted to the rear part.

A calibrated screw cap for the seating of the carbon dioxide cartridge is connected to unit (14). The head of this cartridge is fitted with a needle valve (2) designed to pierce the cartridge. The syringe reservoir (3) contains the solution to be delivered, which is introduced through the opening (12).

The end of the syringe is fitted with a solution suction tube (11) and a spring-loaded ball valve (8) in correspondence with nozzle (7), which is threaded so that the disposable needle (13) can be changed.

The opening mechanism of valve (8) uses a traction cable (10), or other mechanical means with controlled opening more suitable for a particularly specific use.

The opening mechanism is controlled by a trigger (9) inserted in the handgrip of pistol (4), preferably made of a soft material.

In one of the preferred embodiments of the invention the syringe is filled with a formaldehyde aqueous solution in amounts from 100 to 1000 ml, which can delivered by means of the propellant action of the carbon dioxide contained in the ampoule in amounts ranging from 5 to 10 g.

The following examples illustrate the invention in more detail.

EXAMPLE 1

Method for the preparation of pressurised single-dose cartridges able to sterilize water simultaneously with the carbonating action performed by carbon dioxide.

A standard stainless steel cartridge used to make soda water in a specific mixer has a volume of around 10–12 cc, and is typically filled with carbon dioxide with a "technical" purity grade up to saturation point, and a final pressure of about 7.0 MPa.

Under these conditions the cartridge contains 7–10 g of liquefied carbon dioxide, enough to make 1 liter of soda water.

The method proposed consists of introducing into the cartridge a solution of sodium hypochlorite containing 7% w/w of active chlorine, and then filling it with carbon dioxide.

For this exemplified application, it is sufficient for the cartridge to contain approx. 7–15 mg of concentrated solution to obtain a sterilising mixture which, when metered into the mixer containing 1 liter of water, guarantees bactericidal efficiency higher than 99.9%, with contact times of about 30 minutes at room temperature.

EXAMPLE 2

The method proposed involves the previous introduction of a dessicant in powder form (typically 20 mg of oven-dried silica gel) into the empty cartridge described in example 1. The mixture of carbon dioxide and chlorine, previously prepared in the desired ratio into a pressurised tank equipped with a system for drying the gases, will then be introduced.

In the case in example it is sufficient for the cartridge to contain approx. 0.5–1 mg of chlorine to guarantee bactericidal efficiency higher than 99.9% in the mixer containing 1 liter of water, with contact times of about 30 minutes at room temperature, without affecting the odour and taste characteristics of the water.

EXAMPLE 3

Method for preparation of cylinders usable to sterilise water in public distribution plants, or for sterilising swimming pool water. Cylinders with a typical carbon dioxide content of 30 kg and a chlorine content of up to 120–150 g can be prepared for these uses.

Using a cylinder of this kind, it is possible to keep the microbial content of a swimming pool containing about 3000 m$^3$ of water, with average occupancy, under a reliable control for about a week (average weekly dose 0.05 mg of chlorine per liter of water), with bactericidal efficiency higher than 99.9% at room temperature.

EXAMPLE 4

Method for extemporary preparation of disinfectant solutions designed for sanitising articles and surfaces in general. The method proposed involves the introduction of a solution of sodium hypochlorite containing 7% w/w of active chlorine into the cartridge described in example 1, and then adding carbon dioxide.

In the case in example, it is sufficient for the cartridge to contain 1–2 mg of active chlorine to be diluted in the mixer containing 1 liter of water to obtain a disinfectant suitable for sanitising surfaces. This solution exhibits a bactericidal efficiency higher than 98% merely on contact, with contact times of about 30 minutes at room temperature.

EXAMPLE 5

Method for the preparation of a gel with an anti-mould action to be applied to walls and surfaces in general, whether or not they are destined to be painted subsequently.

One of the possible formulations of the method proposed involves mixing the following substances:

Borax: 30 g
Soap powder: 10 g
Silica: 160 g
Aqueous solution of sodium hypochlorite containing approx. 5% active chlorine: 750 ml.
Water: sufficient to make up to one liter.

The mixture obtained, which has the consistency of a gel, is introduced into a spray canister subsequently filled with carbon dioxide to a pressure of 3–7 MPa, and sprayed onto the surface to be treated. The anti-mould effect is immediately evident at the time of application. If the wall shows evident mould, the result will be complete and lasting after 12 hour contact. The total disappearance of mould from the treated wall makes it possible to paint after the removal of the gel.

EXAMPLE 6

The cartridge in example 1 can be used in combination with a pressure syringe.

FIG. 2 schematically illustrates the special syringe in question (with suitable attachments) which can be used to inject the solution.

The cartridge is filled with 500 ml of 40% w/v aqueous formaldehyde and pressurized by screwing the cartridge containing carbon dioxide to a pressure of 1–3 MPa, typically 1.5 MPa.

In this specific case, other propellant gases, such as helium, nitrogen, argon, etc., can be used instead of carbon dioxide whenever it is not considered essential to associate the biocidal function with carbon dioxide.

The cartridge allows very fast, efficient injection of the biocidal solution commonly used in the field of preservation of corpses and anatomical parts.

This method also makes it possible to inject the aqueous formaldehyde directly into natural or artificially made orifices in the human body.

The invention claimed is:

1. A pressurized container for the delivery of a biocide, said container including:
   a mixture consisting essentially of a biocide and carbon dioxide, said carbon dioxide being in the form of a vapour, liquid/vapour mixture or supercritical fluid, wherein said biocide is selected from the group consisting of (1) chlorine gas, (2) chlorine gas and alkali metal hypochlorite, (3) chlorine gas and alkaline earth metal hypochlorite and combinations thereof; and
   said pressurized container having a dispensing spout emitting the mixture, a suction tube extending into the container, and a metering device regulating the emission of the mixture.

2. Container as claimed in claim 1, in which the container contains a desiccant anhydrous salt.

3. Container as claimed in claim 1, which is fitted with a device suitable for delivery and metering in a continuous or discontinuous controlled manner.

4. Container as claimed in claim 1, which is suitable for delivering a single dose.

5. Container as claimed in claim 1, suitable for delivering multiple doses.

6. Container as claimed in claim 1, in which the mixture is in semifluid, paste, gel or solid form.

7. Container as claimed in claim 1, wherein said alkali metal hypochlorite and said alkaline earth metal hypochlorite are sodium hypochlorite and calcium hypochlorite.

\* \* \* \* \*